United States Patent [19]

Larue et al.

[11] Patent Number: 5,507,183

[45] Date of Patent: Apr. 16, 1996

[54] ULTRASONIC METHOD AND APPARATUS FOR DETECTING AND IDENTIFYING CONTAMINATION SUCH AS ICE ON THE SURFACE OF A STRUCTURE

[75] Inventors: Francois Larue, Neauphle Le Chateau; Jërôme Bisson, Le Plessis Robinson, both of France

[73] Assignee: Intertechnique, Plaisir, France

[21] Appl. No.: 223,688

[22] Filed: Apr. 6, 1994

[30] Foreign Application Priority Data

Apr. 7, 1993 [FR] France .................. 93 04126

[51] Int. Cl.⁶ .............. G01N 29/20; G01N 29/18
[52] U.S. Cl. .............. 73/598; 73/600; 73/617; 340/962; 340/582
[58] Field of Search .............. 73/617, 598, 600, 73/170.26, 597, 599, 644, 642, 641, 617, 598, 600, 628, 646, 609, 624, 629; 340/962, 580, 582; 244/134 R, 134 F

[56] References Cited

U.S. PATENT DOCUMENTS

| | | | |
|---|---|---|---|
| 2,419,454 | 4/1947 | Le Clair | 340/582 |
| 2,966,058 | 12/1960 | McSkimin et al. | |
| 3,546,924 | 12/1970 | Nussbaum et al. | 73/627 |
| 3,747,398 | 7/1973 | Rathburn et al. | 73/617 |
| 4,461,178 | 7/1984 | Chamuel | |
| 4,604,612 | 8/1986 | Watkins et al. | 73/599 |
| 4,628,736 | 12/1986 | Kirby et al. | |
| 4,833,660 | 5/1989 | Deom et al. | 73/617 |
| 5,095,754 | 5/1992 | Hsu et al. | |

FOREIGN PATENT DOCUMENTS

| | | | |
|---|---|---|---|
| 284689 | 10/1988 | European Pat. Off. | 73/600 |
| 67164 | 3/1991 | Japan | 73/600 |
| 1117664 | 6/1968 | United Kingdom . | |

Primary Examiner—Hezron E. Williams
Assistant Examiner—Nashmiya Ashraf
Attorney, Agent, or Firm—Larson and Taylor

[57] ABSTRACT

A method and an apparatus for detecting and identifying a contaminant, such as ice, on the surface of a structure, such as a wing, are disclosed. The apparatus has a probe having a delay block with an interface apt to be placed flush with the surface of the structure and two faces at the same angle of inclination relative to the interface and having transmission and reception transducers each oriented perpendicularly to one of the faces. The block has an acoustic impedance lying in the range of 0.7 to 3×10⁶ kg/m².s. It further has an energization and analysis unit for applying an electrical energization pulse to the transmission transducer and comparing the amplitude and the phase of the echo from the interface with a reference echo corresponding to no contamination.

14 Claims, 3 Drawing Sheets

ULTRASONIC METHOD AND APPARATUS FOR DETECTING AND IDENTIFYING CONTAMINATION SUCH AS ICE ON THE SURFACE OF A STRUCTURE

BACKGROUND OF THE INVENTION

The present invention relates to detecting the presence of and identifying a contaminant belonging to a family of known contaminants, the contaminant being on the surface of a structure, and the invention makes use of the difference in acoustic impedance between air and contaminants such as ice.

A major application of the invention lies in aviation, where, during cold periods, it is important to discover prior to aircraft take off whether the surfaces of its lift structures are clean, and, if they are polluted, to determine the nature of the contaminant (ice, mixture of solid and liquid phases, liquid, etc.).

Ultrasonic devices are already known for detecting ice and optionally also for measuring the thickness of a layer of ice. They do not make it possible to identify a contaminant of some other kind that may happen to the present. Unfortunately, prior to aircraft take off, it is important to determine whether the wings are covered by ice which severely and lastingly reduces lift, or whether they are covered of melting snow, of an antifrost or a defrosting liquid, or of a mixture of water and defrosting or antifrost liquid that will be blown away on acceleration.

There is also known (U.S. Pat. No. 2,966,058) a method for measuring dynamic properties of material, wherein the amplitude and phase of acoustic energy shear waves which have traversed a block are compared with the amplitude and phase of waves reflected by a surface of the block which carries a sample of the material.

SUMMARY OF THE INVENTION

It is an object of the invention to make it possible not only to detect the presence of contaminants, but also to discriminate between various possible contaminants. To this end, use is made of the effect of abrupt changes in acoustic impedance at the interface with air if the surface is clean or with the contaminant on reflection of ultrasound waves.

It is known that the acoustic impedance W of a substance is equal to the product of its density multiplied by the speed of sound in the substance. Acoustic impedance has the following values:

$1.4 \times 10^6$ kg/m$^2$.s for water, $1.7 \times 10^6$ kg/m$^2$.s or thereabout for most de-icing and anti-icing liquids; and $4 \times 10^6$ kg/m$^2$.s or thereabout for ice and frost.

The reflection coefficient R and the transmission coefficient D at the interface between two media depend on the impedances W of the media that are separated by the interface. At a zero angle of incidence:

$R = (W_2 - W_1)/(W_2 + W_1)$ $D = 2W_2/(W_2 + W_1)$, where the subscripts 1 and 2 correspond to the media that are upstream and downstream, respectively, in the wave propagation direction.

The coefficients R and D also vary as a function of the angle of incidence on the interface, between the orthogonal incidence and the angle of incidence that corresponds to total reflection.

The invention provides, in particular, a detection and discrimination method according to which a burst of ultrasound is directed towards the interface through a block of material that constitutes a delay line and that has an acoustic impedance that is intermediate between the impedance of liquids and the impedance of ice, the burst being directed at an oblique angle of incidence, and the amplitude and the phase of the echo (reflected waves) are compared with the amplitude and the phase of the incident waves or with the amplitude and the phase of a reference echo as obtained using a clean surface.

The angle of incidence is advantageously selected so as to conserve a high echo power even in the presence of ice on the surface. The echo first falls off from normal incidence after which it increases until it reaches 100% for longitudinal waves beyond total reflection. In practice, an angle of incidence is selected which lies between the angle at which, in the case of ice, the coefficient of reflection is equal to that obtained under a normal angle of incidence and an angle a slightly greater than the angle of total reflection for longitudinal waves. For a material having an acoustic impedance of about 2.85, an angle lying in the range of 35° to 45° will typically give satisfactory results.

In order to detect and discriminate ice, the material from which the block is made is advantageously constituted to present an impedance that is more or less equal to the mean of the impedances of liquids and of ice. In particular, it is possible to use polysulfone (PSU) for which $W = 2.85 \times 10^6$ kg/m$^2$.s and an angle of incidence $\beta$ close to the angle of total reflection at the PSU/ice interface.

Using PSU, at a normal angle of incidence, the following values are obtained:

$R = -0.25$ with a contaminant constituted by a deicing liquid;

$R = -0.34$ with water;

$R = +0.17$ with ice (where the positive value corresponds to a phase inversion); and $R = 0.99$ with air, i.e. with a surface which is clean.

A convenient solution consists in storing the echo obtained from the surface of a "clean" structure, and in particular in measuring the time interval that elapses between the transmission of the burst and the beginning of the echo, and also the amplitude and the sign of the first echo peak when the surface is clean, and then in comparing them with the corresponding magnitudes obtained during successive detection tests (optionally after making corrections to take account of temperature).

In an advantageous embodiment of the invention, the method also makes it possible to determine the thickness of the layer of contaminant, by measuring the time interval between the echo on said interface and the echo on the contact surface between the contamination and air.

The invention also provides an apparatus for detecting and identifying the nature of a contaminant covering the surface of a structure, which contaminant may be ice, the apparatus comprising:

a probe having a delay block with an interface apt to be placed flush with the surface of the structure and two faces at the same angle of inclination relative to the interface and having transmission and reception transducers each oriented perpendicularly to one of the faces, said block having an acoustic impedance lying in the range of 0.7 to $3 \times 10^6$ kg/m$^2$.s, and energization and analysis means enabling an electrical energization pulse to be applied to the transmission transducer and enabling the amplitude and the phase of the echo from the interface to be compared with a reference echo corresponding to no contamination (or with the ultrasound signal that comes from the transmission transducer in the event there is no separate sensor for providing a reference).

The presence of an attenuated interface echo without phase inversion and having a time delay corresponding to the back and forth travel time to the interface then indicates that there is a film of liquid on the surface. An echo with phase inversion is indicative of ice. Very great attenuation of the echo is indicative of the presence of a contaminant having acoustic impedance close to that of the delay block, i.e. of melting snow (sludge), of a mixture of water and ice crystals, etc.

The device may also be designed to measure the thickness of ice. To do this, the energization and analysis means are designed also to measure the time interval between the echo on the interface and the echo on the outer face of the layer of ice.

The apparatus may include self-testing means that verify the presence of an echo responsive to each energization of the or each transmission transducer.

The invention also relates to other dispositions advantageously usable in combination with the above dispositions, but capable of being used independently. All of the dispositions will appear more completely on reading the following description of an embodiment, given by way of non-limiting example. The description refers to the accompanying drawings.

DETAILED DESCRIPTION

Figure 1:
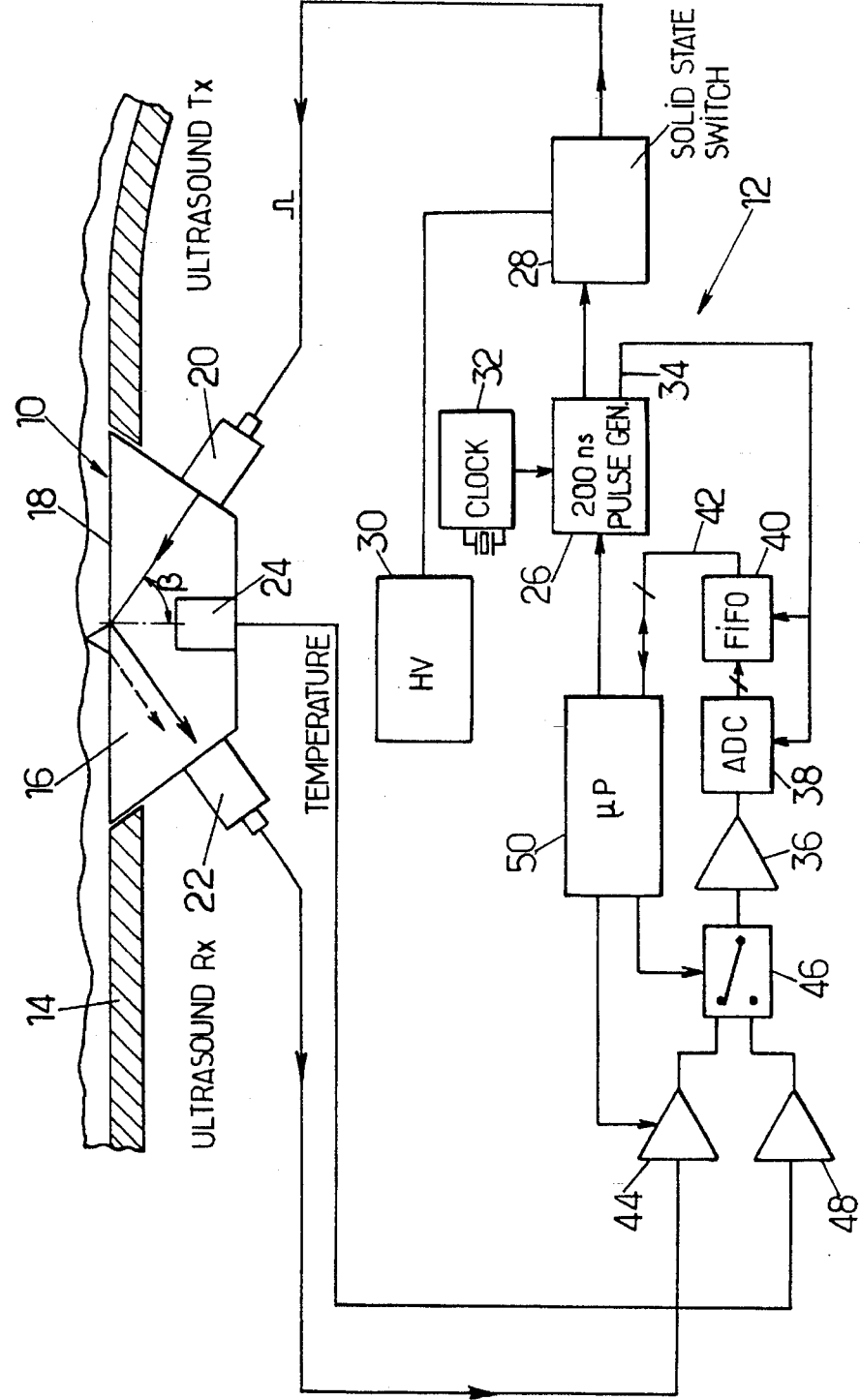
FIG. 1 is a block diagram of apparatus constituting a particular embodiment of the invention.

The apparatus whose basic structure is shown in FIG. 1 may be considered as comprising a probe 10 and an energization and analysis unit 12. Actually, the energization and analysis unit is often associated with a plurality of probes 10 and performs successive detection operations via different probes, cyclically.

The probe 10 is designed to be mounted in a structure so that its interface with the ambient medium is flush with the outer surface of the structure 14. It includes a block 16 designed to constitute a delay line, made of a material whose acoustic impedance is intermediate between the impedance of ice and the impedance of liquids, and is therefore close to the impedance of a mixture of liquid and solid phases. In particular, it is possible to use polysulfone (PSU) whose acoustic impedance is about $2.85 \times 10^6$ kg/m$^2$.s. The block 16 generally has a plane interface 18, e.g. in the form of a circle having a diameter of one to a few centimeters. However, the interface may be bulged, in particular to fit over the structure when fitted with the apparatus. It has two oblique faces that are symmetrical about a mid-plane of the block 18 and that are designed respectively to receive a transmission transducer 20 and a reception transducer 22. The faces and the transducers are oriented so that the angle of incidence $\beta$ is close to the critical angle for an interface with ice. In practice, the angle of incidence $\beta$ generally lies in the range 40° to 55°.

The transducers 20 and 22 are generally constituted by piezo-electric transducers with heavy damping, that are designed, when excited by a single pulse, to deliver an ultrasound burst constituted by a damped alternating wavetrain. In particular, it is possible to use transducers that have a resonant frequency of about 2 MHz. The cross-section of the transducers is selected in particular as a function of the maximum thickness of ice that it is desired to measure. In practice, with an angle $\beta$ of about 45° and with transducers having an active element with a diameter of 6 mm to 7 mm (and an emissive surface with a diameter of about 10 mm) it is possible to measure a thickness of ice of up to about 3 mm.

It will be shown that the discrimination and the measurement of thickness are improved by performing a temperature correction which requires knowledge of the temperature of the block 16. Consequently, the block may have embedded therein a temperature probe 24 whose function appears below.

The energization and analysis unit 12 is designed to apply an electric pulse of predetermined amplitude and duration to the transmission transducer 20 and to analyse the ultrasound echo received by the transducer 22.

The energization unit includes a transmission channel connected to the transducer 20. In the embodiment as shown, this channel comprises generator 26 of short pulses (e.g. 200 nanosecond duration pulses) controlling the closing of an electronic switch 28 that is connected to a high voltage source 30. The generator may be provided with a clock 32 that sets the duration of the pulses, and it may include a frequency divider making it possible to use an output 34 for distributing a clock signal, e.g. at a frequency of 20 MHz, for sampling the echo.

The transducer 20 may be of a type that is commonly available on the market, and that is compact (e.g. having a diameter of 7 mm and a length of 13 mm). It is heavily damped, such that the delivered ultrasound amplitude peaks decrease quickly in time. To detect ice, transducers having a resonant frequency of about 1 MHZ to 3 MHz, delivering longitudinal waves, generally give satisfactory results.

The unit also includes a reception channel having an amplifier 36, an analog digital converter (ADC) 38 having a sampling rate that is much greater than the resonant frequency of the transducers (e.g. ten times said frequency) and a memory 40 organized as a first in-first out stack), and connected to a data bus 40. Operation of the ADC 38 and of the memory 40 is synchronized by the clock signal from output 34.

The embodiment shown in FIG. 1 is designed to perform scale correction and a correction responsive to temperature. To this end, it includes a controlled pregain-amplifier 44 between the transducer 22 and the fixed gain amplifier 36. A switch 46 makes it possible, at will, to connect the reception channel either to receive the output signal from the amplifier 44 or else to receive the output signal from a fixed gain amplifier 48 that is connected to the temperature sensor 24.

The operation of the unit 12 is controlled by a computing unit 50 comprising a microprocessor and memories, and that also serves to analyse the signals. This computing unit enables each measurement to be initiated by sending a start signal to the generator 26. It also enables the switch 46 to be operated so as to measure the operating temperature. As a function of the difference between a calibration temperature and the temperature during the measurement, it takes account of changes in the velocity of sound by using a correction table stored in memory.

Before being used to detect the possible formation of ice, the apparatus as described above is subjected to a calibration step which may be performed once for all or which may be repeated at regular intervals under conditions where the surface is clean.

During calibration, a pulse is transmitted and the echo signal is analysed over a period of time that covers at least the first two alternations of the received signal (when performing detection only) or until the first alternation of the echo signal from the outer surface of a layer of contaminant having the maximum measurable thickness (when the apparatus is also used for measurement). The following instants are observed: $R_1$, marking the beginning of the echo signal; $R_2$, marking the first zero crossing; and $R_3$, marking the second zero crossing. The measurement temperature is also stored.

A new calibration may be performed immediately before each series of measurements, while the structure is sheltered and therefore, in theory, not polluted. If the same values are obtained for $R_1$, $R_2$ and $R_3$, then it is confirmed that the probe is clean. Otherwise, the stored values of $R_1$, $R_2$ and $R_3$ are used. Insofar as the probe is clean, the suitably programmed computing unit adjusts the gain of the preamplifier 44 so that the amplitude of the highest peak in the signal received by the ADC 38 corresponds to full-scale. The amplitude $A_0$ of the first peak, at least, is also stored.

Calibration may include a sequence of several identical operations, the stored values then being constituted by averages, e.g. taken on ten successive tests.

When performing detection proper, the computing unit 50 first measures temperature, by appropriately switching the switch 46, thereby making it possible to compensate for variation in the velocity of ultrasound waves through PSU as a function of temperature, by referring to a stored look-up table. Thereafter, the transmission transducer 20 is energized by a pulse. The relevant periods of time are the period from $t_0$ to $t_1$ for detection purposes, and beyond $t_2$ for measuring thickness (where $t_2$ designates the time of flight between transmission and reception for the minimum thickness that it is deemed necessary to measure).

Figure 2:
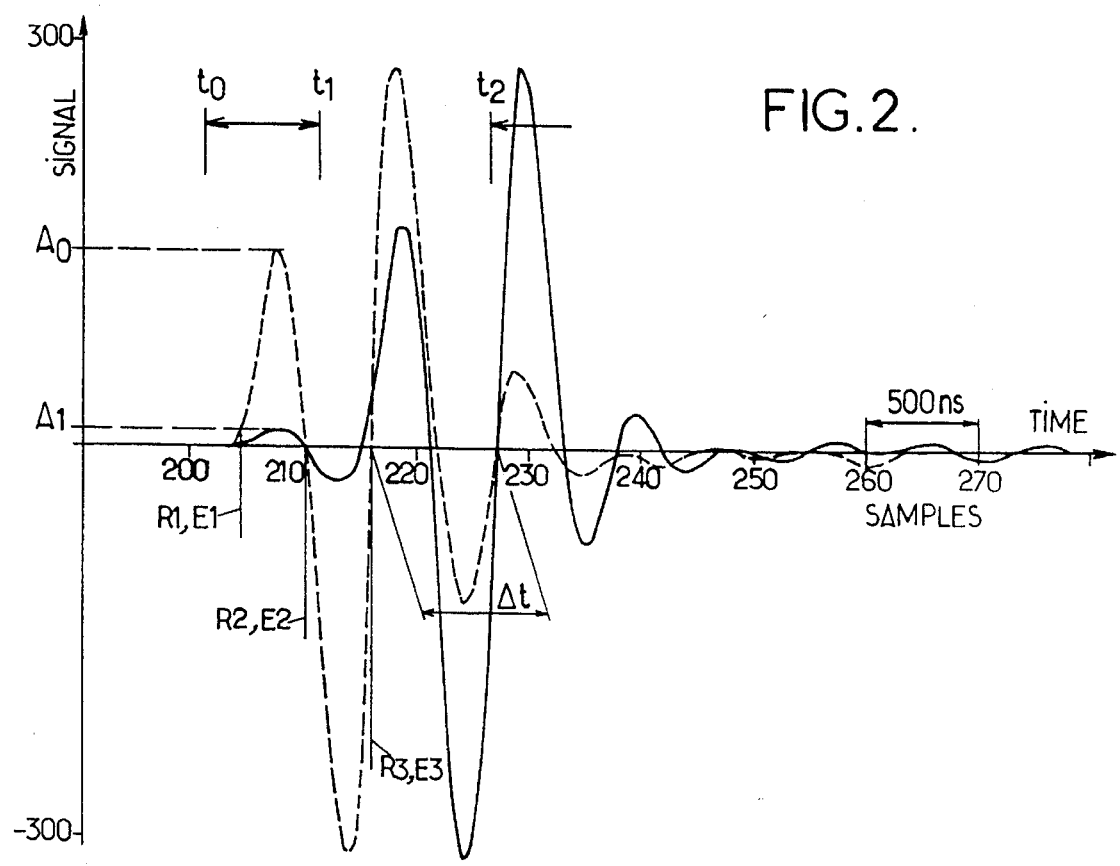
FIG. 2 is a training diagram where dash-lines show the appearance of an echo signal obtained from a clean surface and solid lines show an echo signal obtained from a surface carrying a film of anti-icing liquid.

The solid line curve of FIG. 2 constitutes an example showing a signal as obtained when there is a 0.44 mm thick film of anti-icing liquid on the surface of the probe. Under such circumstances, zero crossings take place at instants $E_1$, $E_2$ and $E_3$. The computing unit is also designed to measure the amplitudes of the first peaks together with their signs, and to compare them with the stored amplitude of peaks as obtained when the probe is "clean". Insofar as temperature has not changed since calibration, the points $R_1$ and $E_1$ coincide. If there has been a change of temperature, then a temperature correction performed by the computing unit serves to bring them back into coincidence.

If an anti-icing liquid (e.g. ethylene-glycol) is present, then the first peak has the same phase as for a clean probe (Fig.2), thus indicating that the contaminant is a liquid, but its amplitude $A_1$ is much less than the amplitude $A_0$ because the impedance discontinuity is much less marked than it is with a clean probe. The locations of the peaks may be identified by detecting the zero crossings of the derivatives of the curve. The computing unit may be designed to indicate the presence of liquid when the ratio $A_1/A_0$ lies within a determined range, without a change of sign.

The apparatus may also be designed to measure the thickness of the film of liquid. To do this, the time delay is measured between the appearance of the first echo peak from the surface of the film and the first echo peak from the interface. This delay $\Delta t$ corresponds to the back and forth travel time through the film at an angle of incidence that is known. The thickness of the film can be deduced therefrom, being about 0.4 mm in the example shown in FIG. 2.

Figure 3:
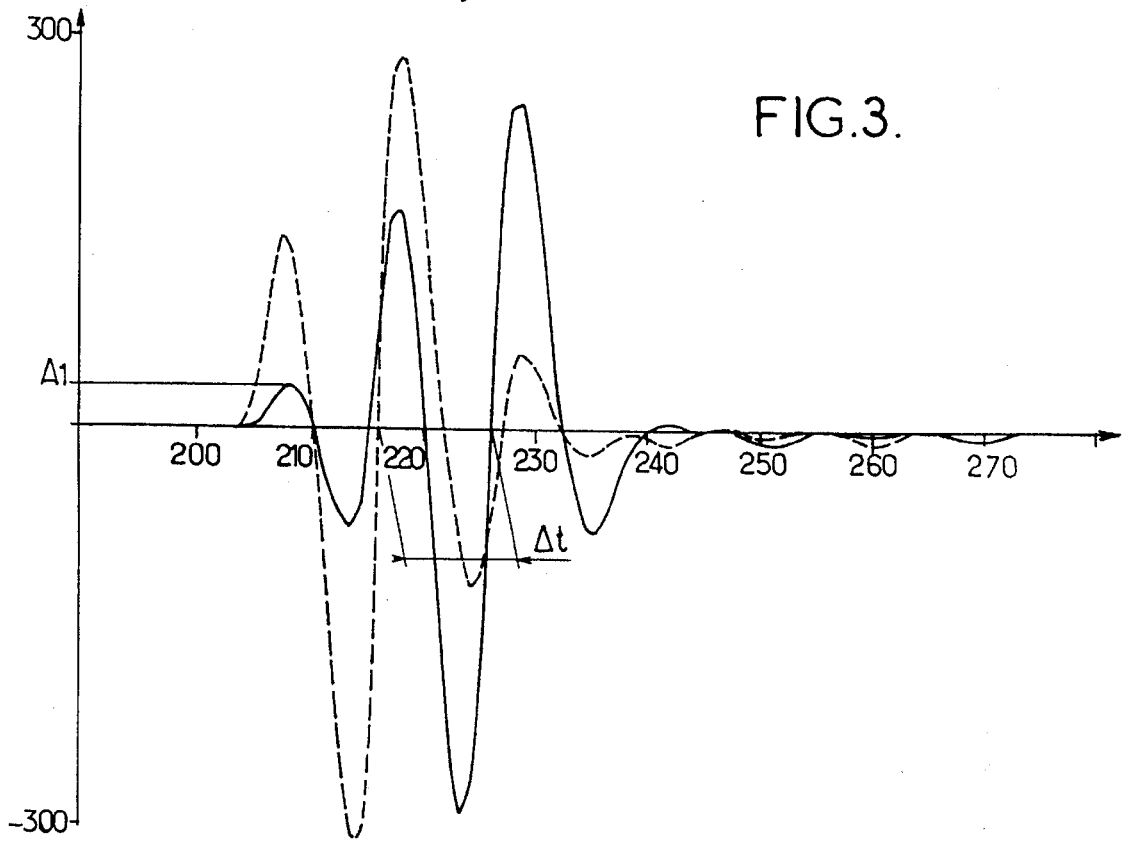
FIGS. 3, 4 and 5 are similar to FIG. 2 and correspond respectively to the presence of a mixture of water and defrosting liquid, to the presence of melting snow or "slush", and to the presence of ice.

In the example shown in FIG. 3, the film is constituted by a mixture of water and of anti-icing fluid. Under such circumstances, the attenuation is less than for antiicing fluid alone, since the reflection coefficient at normal incidence is −0.34 for water, whereas it is −0.25 with the fluid.

In this case, the delay $\Delta t$ corresponds to the presence of a film of water-fluid mixture having a thickness of about 0.37 mm.

Figure 4:
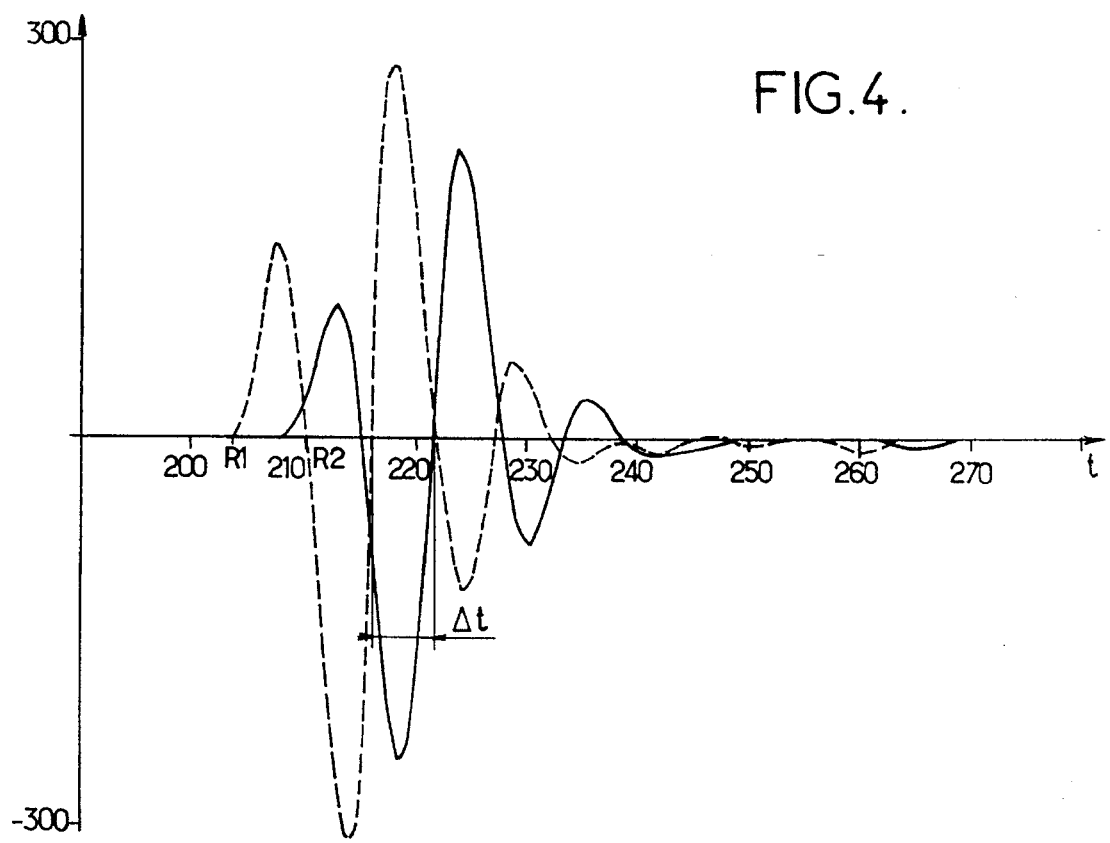

The case shown in FIG. 4 corresponds to the presence of melting snow, which has an acoustic impedance very close to that of PSU. Consequently, that is a loss of echo at the interface. It nevertheless remains possible to derive the thickness of the film of contamination from time interval $\Delta t$. In the example shown in FIG. 4, the thickness is about 0.5 mm.

Figure 5:
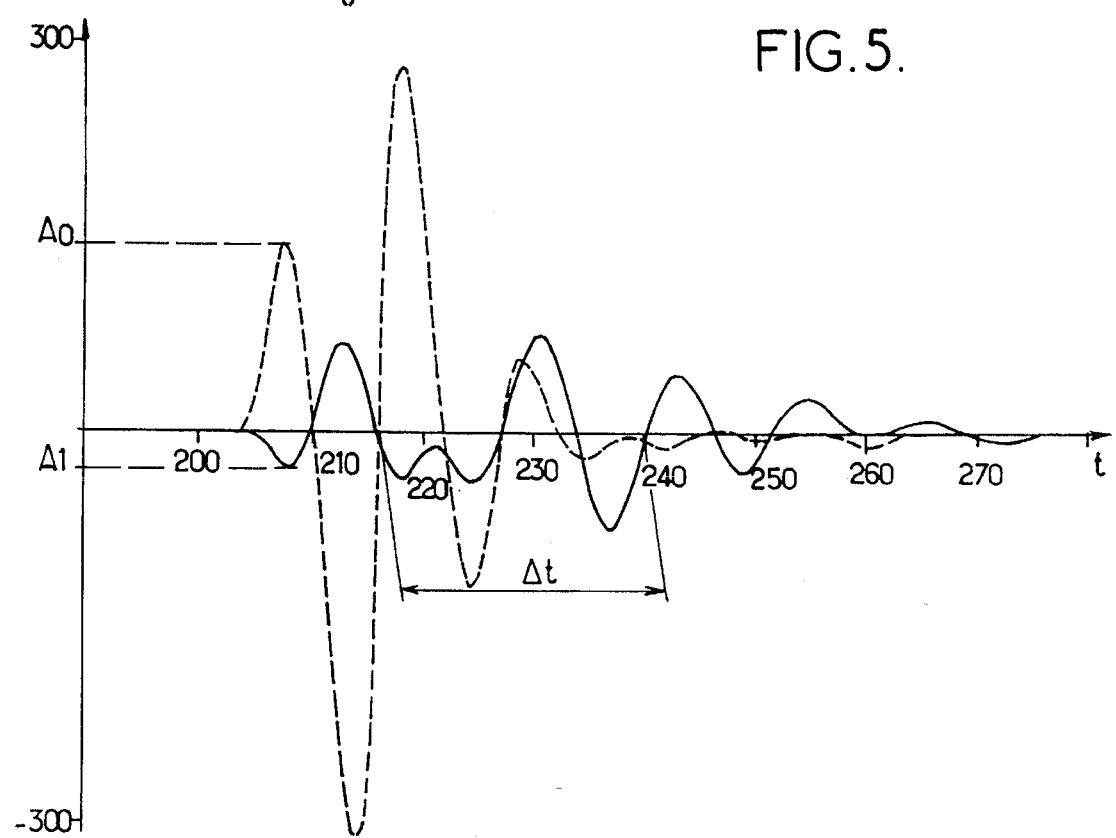

Finally, in the case shown in FIG. 5, ice is present on the probe 10. In this case, reflection at the interface is accompanied by a change of phase, and the first peak of amplitude $A_1$, is opposite in polarity to the peak $A_0$ of the echo signal from the sensor when clean.

Here again, it is possible to measure the ice thickness on the basis of the time interval $\Delta t$, which thickness is about 2.4 mm in the example shown in FIG. 5. Under such circumstances, reflections at the interface and at the surface of the film of ice gives rise to peaks of opposite polarity.

In all of the examples described above, it is advantageous to perform a sequence of a plurality of successive measurements and to display the average of the results, thus making it possible to take better account of temporarily known uniformities in the surface. Measurements remain possible as long as the thickness is not such that the energy refracted at the interface no longer reaches the reception transducer 22. Using transducers having an active diameter of about 6 mm or of about ¼ in, is generally possible to measure a thickness of up to about 3 mm.

Figure 6:
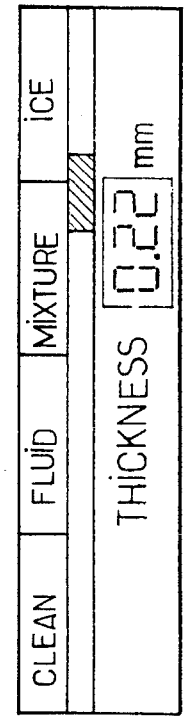
FIG. 6 shows one possible form of display.

As shown in FIG. 6, the display may be formed by moving a coloured area along a scale and by giving a digital indication of thickness.

We claim:

1. Apparatus for detecting and identifying the nature of a contaminant covering a surface of a structure, comprising:

a probe having a delay block with an interface apt to be placed flush with said surface of said structure and two faces having a same angle of inclination relative to the interface and having transmission and reception transducers each oriented perpendicularly to a respective one of the faces, said block being of a material having an acoustic impedance lying in the range of 0.7 to $3 \times 10^6$ kg/m$^2$.s, and energization and analysis means for applying an electrical energization pulse to the transmission transducer and comparing the amplitude and phase of an echo from the interface with a reference echo obtained when there is no contaminant on said interface to thereby detect and identify the nature of any contaminant on the surface.

2. Apparatus according to claim 1, further comprising self-testing means constructed to check whether there is an echo responsive to each energization of said transmission transducer.

3. Apparatus according to claim 1, wherein said energization and analysis means are constructed to measure a time interval between the echo at said interface and a reference echo due to a reflection on an outer surface of the contaminant, if present, and to derive a thickness of said contaminant from said time interval.

4. Apparatus according to claim 3, further comprising means for measuring a temperature of the delay block and means for correcting said time interval responsive to said temperature.

5. Apparatus according to claim 1, wherein the block is made of polysulfone.

6. Apparatus according to claim 1, wherein said faces of said block have a slope such that acoustic waves from said transmission transducer have an angle of incidence close to the total reflection angle on said interface with ice, for longitudinal waves.

7. Apparatus according to claim 1, wherein said energization and analysis means comprise means for storing a reference echo obtained with a clean interface.

8. Apparatus according to claim 1, wherein said transmission transducer is a dampened transducer and said energization means are arranged for delivering short pulses to said transmission transducer.

9. Apparatus for detecting and identifying the nature of a contaminant belonging to the group consisting of ice, water, defrosting liquids, slush and mixtures thereof covering a surface of a structure, comprising:

a probe having
  a delay block of polysulfone with an interface apt to be placed flush with said surface of said structure, constituting an interface with any said contaminant, and with two faces, said faces having a same angle of inclination of from 40° to 55° relative to the interface,
  a transmission transducer oriented perpendicularly to one of said faces and in contact therewith;
  a reception transducer oriented perpendicularly to the other one of said faces and in contact therewith;
energization means for applying an electrical energization pulse to the transmission transducer; and
analysis means for comparing the amplitude and phase of an echo signal delivered by said reception transducer and due to an echo on the interface with a reference echo signal obtained when there is no contaminant on said interface; and
storage means for storing said reference echo signal whereby the analysis means detects and identifies the nature of any contaminant present.

10. A method for detecting and identifying the type of contaminant on an outer surface of a structure, comprising the steps of:

(a) directing a burst of incident ultrasound waves through a block of material to a surface of said block flush, with said outer surface and constituting an interface with any said contaminant present on said structure, said block constituting a delay line and having an acoustic impedance that is intermediate between impedances of liquids and the impedance of ice, the burst being directed at an oblique angle of incidence with respect to said interface;

(b) receiving an echo formed at said interface;

(c) comparing an amplitude and a phase of said echo with an amplitude and a phase of the incident ultrasound waves or with an amplitude and a phase of a reference echo as obtained from a clean said interface; and (d) identifying the type of contaminant, if present, from both comparisons of step (c).

11. Method according to claim 10, further comprising a preliminary calibration step of forming and storing said reference echo obtained at said interface when clean and of measuring the amplitude and phase of a first peak of said reference echo.

12. Method according to claim 10, further comprising measuring a time interval separating a first peak of the echo received during step (b) and a first peak of any additional echo at another surface separating said contaminant on said structure, if present, and ambient.

13. Method according to claim 10, wherein said contaminant is identified as ice upon finding that the phase of a first peak of said echo formed at said interface is opposite to the phase of a first peak of said reference echo, said contaminant is identified as a liquid upon finding there is no change of phase of the first peak of the echo and the amplitude of said echo at said interface is decreased as compared with said reference echo, and said contaminant is identified as melting snow or sludge upon finding that the amplitude of a first peak of said echo formed at said interface is reduced substantially to zero.

14. Method according to claim 11, comprising, during the calibration step, detecting and storing a beginning, a first zero crossing and a second zero crossing of the echo at said interface.

* * * * *